United States Patent [19]

Leschinsky et al.

[11] Patent Number: 5,312,352
[45] Date of Patent: May 17, 1994

[54] BUBBLE-FREE CONNECTOR FOR LIQUID CARRYING TUBING

[75] Inventors: Boris Leschinsky, Waldwick; Robert B. Schock, Sparta; Robert L. Wilcox, Wanaque; Clifford E. Schwartz, Maplewood, all of N.J.

[73] Assignee: Datascope Investment Corp., Montvale, N.J.

[21] Appl. No.: 5,334

[22] Filed: Jan. 19, 1993

[51] Int. Cl.⁵ ............................................... A61M 5/00
[52] U.S. Cl. ................................... 604/122; 285/924; 604/905; 604/283
[58] Field of Search ................ 604/905, 122, 283.1, 604/284, 280, 265; 285/153, 924; 137/136

[56] References Cited

U.S. PATENT DOCUMENTS

| | | | |
|---|---|---|---|
| 2,597,699 | 5/1952 | Bauer | 604/122 |
| 3,833,013 | 9/1974 | Leonard | 604/122 |
| 4,143,423 | 3/1979 | Steunlieb | 604/265 |
| 4,361,380 | 11/1983 | Marazzi | 285/924 |
| 4,493,705 | 1/1985 | Gordon | 604/122 |
| 4,526,572 | 7/1985 | Donnan et al. | 604/283 |
| 4,568,333 | 2/1986 | Sawyer | 604/122 |
| 4,615,694 | 10/1986 | Raines | 604/406 |
| 4,636,196 | 1/1987 | Tsuji et al. | 604/905 |
| 4,643,713 | 2/1987 | Vitala | 604/122 |
| 4,863,452 | 9/1989 | Irmiter | 604/122 |
| 5,135,264 | 8/1992 | Elliott-Moore | 285/924 |
| 5,147,298 | 9/1992 | Turner | 604/284 |

*Primary Examiner*—Jerome L. Kruter
*Attorney, Agent, or Firm*—Fitzpatrick, Cella, Harper & Scinto

[57] ABSTRACT

A system and method for connecting two fluid carrying tubes includes a first tube having a lumen therethrough and an open end, and a bubble elimination port proximate the open end and in fluid communication with the lumen, and a second tube having a lumen therethrough and an open end. The first and second tubes are connected in a first position, wherein the lumen of the first tube and the lumen of the second tube form a fluid-tight circuit and the bubble elimination port is open to the circuit, to eliminate any bubbles in the fluid circuit. The first and second tubes then are connected in a second position, wherein the lumen of the first tube and the lumen of the second tube form a continuous, fluid-tight circuit and the bubble elimination port is closed to the fluid circuit.

34 Claims, 4 Drawing Sheets

BUBBLE-FREE CONNECTOR FOR LIQUID CARRYING TUBING

BACKGROUND OF THE INVENTION

1. Field of the Invention

The present invention relates generally to a method and apparatus for connecting two or more fluid carrying tubes. More particularly, it relates to a method and apparatus for connecting blood carrying medical tubing in a continuous fluid circuit without introducing bubbles or other environmental contaminants into the tubing.

2. Description of the Prior Art

Extracorporeal procedures are well known. In these procedures, blood generally is withdrawn from a patient through cannulation, treated (e.g. by pumping, oxygenation, filtering, or the like), and reintroduced to the patient through cannulation. For example, in a cardio-pulmonary bypass procedure, blood may be withdrawn through cannulation at a first site, oxygenated upstream, and reintroduced through cannulation at a second site.

In preparing to perform one of these extracorporeal procedures, one blood carrying tube must be connected to another blood carrying tube. It is important in making this connection to avoid introducing air or other contaminants into the fluid circuit. In particular, air bubbles can cause an embolism or other medical complications that may be fatal to the patient.

Before initiating an extracorporeal procedure, each of the blood carrying tubes typically is primed with a conventional priming fluid, such as a saline-based priming solution, and then clamped at a location proximate the end portion thereof, to assure that each is filled as full as possible with such fluid. The open ends of the primed tubes are then slowly connected together while a syringe or other device provides a continuous stream of solution to the connection site. A variation of this technique may be used when the fluid circuit includes a roller-type pump. In this variation, a perfusionist rotates the pump head of the pump in a forward direction to perform a "roll-up" technique, which continuously advances priming fluid out of the blood tube during the connecting stage.

These techniques have a number of drawbacks. First, each technique requires a degree of training to make a bubble free connection. For example, in the former technique, connection under a stream of fluid may cause air entrainment, resulting in bubbles in the tubing. The latter technique is limited to a roller-type pump, and may not be used with a centrifugal pump, or the like. Each of these techniques requires two people to perform the connection. In addition, since these procedures rely upon flowing fluid to keep air out, they tend to be messy since some of that flowing fluid necessary escapes from the system. Also, after completion of the connection, it often is not possible to disassemble the cannula and tubes if bubbles then are detected in the tubes. Moreover, these techniques are not easily repeatable, and are difficult to perform under emergency conditions.

It is also known in the art to use a connector tube for connecting the open ends of two-fluid carrying tubes. Such a connector tube preferably is a short, rigid cylindrical tube, and may include securing structure, such as barbs, at each end for securely connecting the previously open ends of the fluid carrying tubes to form a closed fluid channel or circuit.

An improvement on this technique includes a hard, barbed, connector tube provided with a branch or side-arm luer port. The luer port may be used for collecting and eliminating any air bubbles trapped in the fluid circuit after connection.

These techniques also have a number of drawbacks. Initially, when a connector tube is inserted in the open end of one fluid carrying tube, it functions as an extension of that tube for connecting to the second tube. Thus, this system includes all of the above-discussed drawbacks. The branches or luer fittings also have a drawback in that they introduce an element that protrudes from the fluid circuit during procedure. This protrusion may catch on surrounding objects or accidentally be broken off, resulting in inconvenience or possibly major blood loss during procedure. Moreover, these protrusions form vestiges that remain on the side wall of the connector tube of the fluid circuit. These vestiges are discontinuities that form stagnation zones in the fluid circuit that tend to cause thrombi.

SUMMARY OF THE INVENTION

The present invention overcomes these and other drawbacks of the prior art by providing a novel method and apparatus for connecting two or more fluid carrying tubes to form a continuous, bubble-free closed circuit.

In one aspect, the present invention relates to a method and system for connecting two or more fluid carrying tubes in a continuous, fluid-tight, bubble-free circuit. The system generally includes a first tube having bubble elimination means proximate an open end thereof, a second tube having an open end, and means for connecting the open ends of the first and second tubes. In a first position, the bubble elimination means is uncovered thereby permitting the escape of gas so as to eliminate any bubbles from the fluid circuit. In a second position, the bubble elimination means is covered so that the bubble elimination means is isolated from the fluid-tight closed circuit.

In one embodiment, the bubble elimination means is a side port and the second tube includes a connector portion which is insertable in the open end of the first tube to form a fluid-tight closed circuit.

In this embodiment, the method of the present invention generally includes the steps of inserting the connector portion of the second tube into the open end of the first tube to the first position. In this first position, the bubble elimination port is uncovered. Bubbles are then eliminated from the circuit, e.g., by venting them to, or trapping them in, the bubble elimination port. The connector portion is then further inserted into the first tube to a second position, wherein the bubble elimination port is covered.

The connecting means may also be a separate connector tube having one end for connecting to the open end of the first tube, and a second end for connecting to the open end of the second tube. The connecting tube may include securing means, such as barbs, at each end. The connecting tube also may have an elongated first end sequentially insertable to first and second positions within the first tube. Moreover, the elongated portion may be lubricated to facilitate insertion.

The first tube may also be provided with a curved portion proximate the open end thereof, and the bubble elimination port may be located at a high point on the curved portion to facilitate bubble elimination. In addition, the curved portion of the first tube may be made of a flexible material, so that the curved portion of the fluid tube may conform to the configuration of a connector portion or tube when the connecting means is connected in the second position.

In yet another embodiment of the present invention, the first tube may include a receiving portion located proximate the open end thereof, and the receiving portion may be pretreated for receiving the connecting means. For example, the receiving portion may be pre-stretched or, the first tube may be formed of a heat sensitive material, and the receiving portion may be preheated to soften the material for receiving the connecting means.

These and other attendant features and advantages of the present invention will be readily and more completely appreciated with reference to the following detailed description of several embodiments taken together with the accompanying drawings.

DETAILED DESCRIPTION OF A PREFERRED EMBODIMENT

Figure 1:
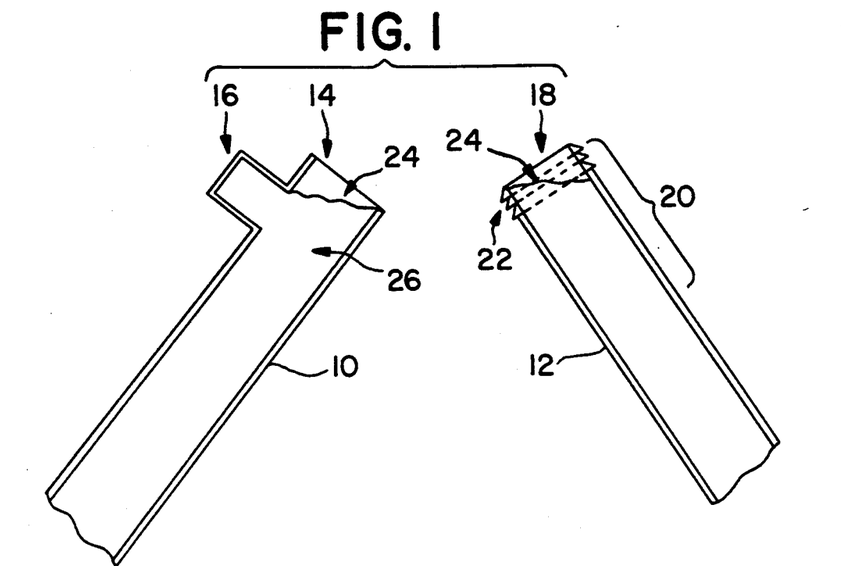
FIG. 1 is side schematic view of one embodiment of a bubble-free connector system of the present invention in an open configuration.
Figure 2:
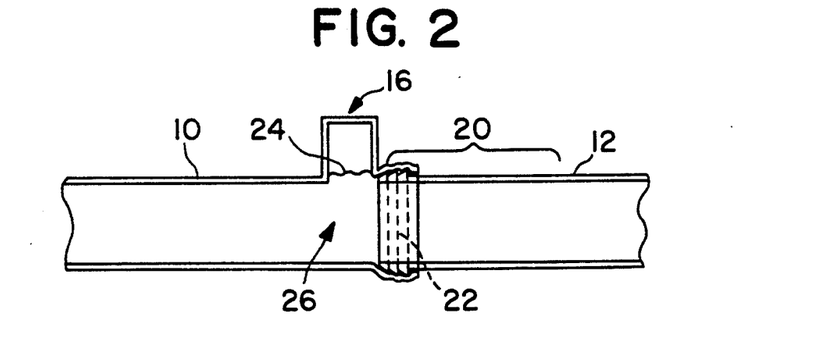
FIG. 2 is a side schematic view of the connector system of FIG. 1, wherein a connector portion of the second tube is inserted to a first position, and a bubble elimination port of the first tube is open to a fluid-tight circuit.
Figure 3:
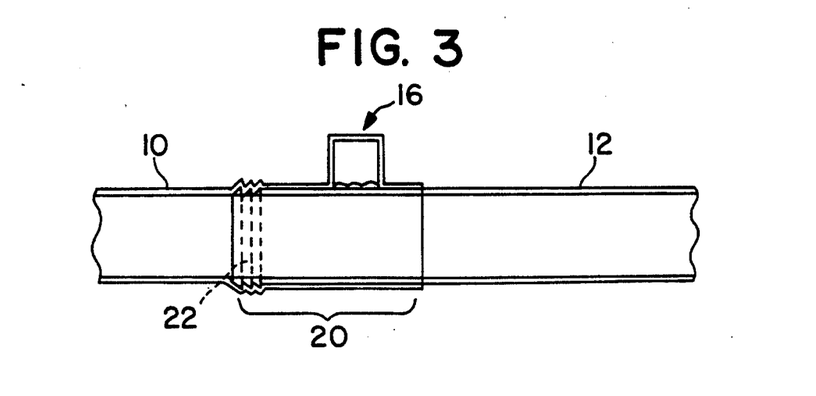
FIG. 3 is a side schematic view of the connector system of FIG. 1, wherein a connector portion of the second tube is inserted to a second position, and a bubble elimination port of the first tube is closed and isolated from the continuous, fluid-tight circuit.

FIGS. 1 to 3 illustrate in side schematic view one embodiment of a connector system of the present invention. The system generally includes a first tube 10, a second tube 12, and means for connecting the first tube 10 and the second tube 12 in a continuous, fluid-tight, bubble-free fluid circuit. More specifically, in the present embodiment, first tube 10 has an open end 14 and a bubble elimination port 16 located proximate open end 14. Second tube 12 has an open end 18 and a connector portion 20 constituting the connecting means.

Each of first tube 10 and second tube 12 is composed of a conventional material suitable for carrying blood. At least one of first and second tubes 10,12 preferably is formed of a flexible plastic material, and most preferably of a clear plastic material, such as Tygon ™ tubing, so that a clinician may view the interior of the tubing to detect any bubbles therein.

In the embodiment of FIGS. 1 to 3, first tube 10 is a ⅜ inch inner diameter—9/16 inch outer diameter tube composed of polyvinylchloride ("PVC"). Bubble elimination port 16 is formed integrally with first tube 10, may have a volume of about 1 cc, and may be located about ¼ inch from open end 14. Second tube 12 is a ⅜ inch inner diameter—9/16 inch outer diameter tube composed of PVC, and connector portion 20 is an extension of this tube having a ⅜ inch inner diameter—9/16 inch outer diameter. Connector portion 20 preferably is about 1 inch long and includes one or more annular ridges or barbs 22 proximate open end 14 of second tube 12. For example, as shown in FIGS. 1 to 3, connector portion 20 may have 3 barbs located in a ¼ inch long portion adjacent open end 14. As will be described below, the sizing of connector portion 20 and barbs 22 is selected so as to provide a fluid tight seal with first tube 10.

A preferred method of the present invention also will be described with reference to FIGS. 1 to 3. Initially, in a priming stage, as shown in FIG. 1, first and second tubes 10,12 are arranged in an orientation wherein the open ends 14,18 thereof are elevated, and tubes 10,12 are primed by a conventional method so that each tube is substantially filled with priming fluid 24 (see FIG. 1). Most preferably, first tube 10 is filled so that bubble elimination port 16 is substantially filled with priming fluid 24. Of course, this may be facilitated by rotating first tube 10 about its longitudinal axis.

Referring to FIG. 2, in a connecting stage, connector portion 20 of second tube 12 then is inserted into open end 14 of first tube 10. Specifically, connector portion 20 is inserted into first tube 10 until it reaches a first position where first and second tubes 10,12 form a closed, fluid-tight circuit, and bubble elimination port 16 is open to the fluid circuit. In this manner, a fluid-tight annular seal is formed between barbs 22 and the inner wall of first tube 10.

It will be appreciated that this connecting stage or procedure generally will trap a small bubble within the fluid circuit proximate connector portion 20, and that the size of the bubble will vary for each procedure, depending on the size of the tubing and the expertise of the clinician. Although it is preferable to form the connection with a minimal sized bubble entrapped therein, it also will be appreciated that bubble elimination port 16 permits a clinician to rapidly and efficiently connect first and second tubes 10,12 without worrying about effecting a bubble free connection in the first instance. Specifically, any bubble entrapped in the fluid circuit at this time then may be eliminated by removing it to bubble elimination port 16. Of course, as a bubble is removed from the fluid circuit to port 16, it will displace an equal amount of fluid from port 16 into the fluid circuit, thereby to eliminate any bubbles in the fluid circuit.

Referring now to FIG. 3, in a final stage, after any bubble entrapped in the fluid circuit is removed to bubble elimination port 16, connector portion 20 further is advanced into first tube 10, to a second position, wherein first and second tubes 10,12 form a continuous, closed, fluid-tight channel or circuit, and bubble elimination port 16 is sealed off from the fluid circuit. In the second position, barbs 22 of connector portion 20 form a fluid-tight annular seal with a portion of first tube 10, upstream of bubble elimination port 16. In other words, bubble elimination port 16 is isolated from the fluid circuit.

The size and configuration of bubble elimination port 16 may vary depending on the particular application or procedure. In its simplest form, as shown in FIGS. 1 to 3, bubble elimination port 16 is merely a collection chamber formed by a convex protrusion in a sidewall of tube 10. The chamber of bubble elimination port 16 has a particular volume and communicates with the lumen 26 of tube 10, for collecting any bubbles that may form in the fluid circuit during the connection procedure. For example, in the embodiment of FIGS. 1 to 3, the volume may be in the range of about 0.5 to 2 cc., and preferably is about 1 cc. Those skilled in the art readily will be able to select the shape and volume of bubble elimination port 16 to suit any given application.

Figure 4:
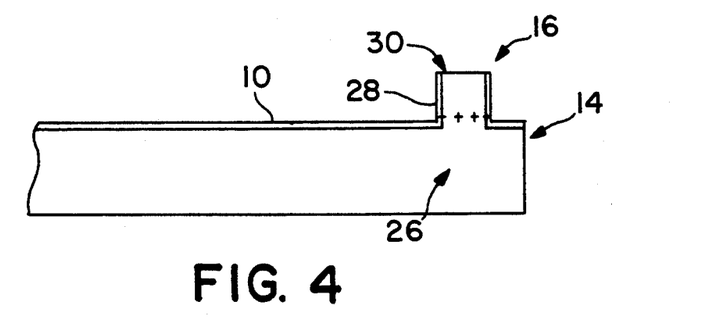
FIG. 4 is a side schematic view of an alternative embodiment of the bubble elimination port of the present invention, including a vent to the exterior environment.

In other embodiments, as shown in FIGS. 4 to 7, bubble elimination port 16 may include a chamber body 28 and a vent 30, for communicating with the external environment. In their simplest form, as shown in FIG. 4, chamber body 28 is generally cylindrical or tubular, and vent 30 is formed by truncating a distal end thereof.

Figure 5:
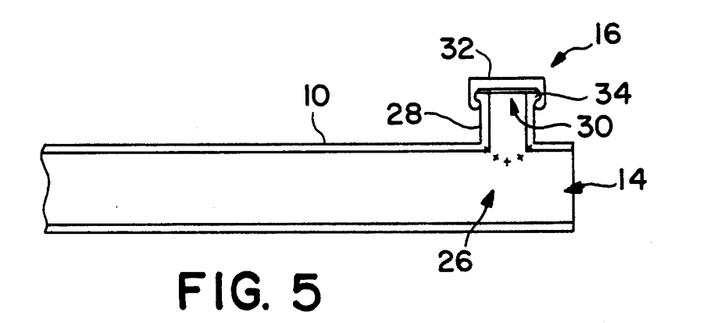
FIG. 5 is a side schematic view of another embodiment of the bubble elimination port of the present invention, including a removable cap.

Alternatively, as shown in FIG. 5, bubble elimination port 16 may be provided with a cap 32. Cap 32 may be removable but securely attachable to chamber body 28 by conventional means, such as a lip 34 formed at the open distal end thereof. It will be appreciated that removable cap 32 may facilitate the above-described procedure for using the system, either by venting bubble elimination port 16 during the priming stage (see FIG. 1), by subsequently venting bubble elimination port 16 during the connecting stage (see FIG. 2), or both. It also will be appreciated that, for a particular application, in this embodiment the volume of bubble elimination port 16 may be significantly smaller than in the embodiment of FIGS. 1 to 3, because any bubbles entrapped in port 16 may be vented to the external environment to allow additional bubbles in the fluid circuit to be removed to port 16 and vented.

Figure 6:
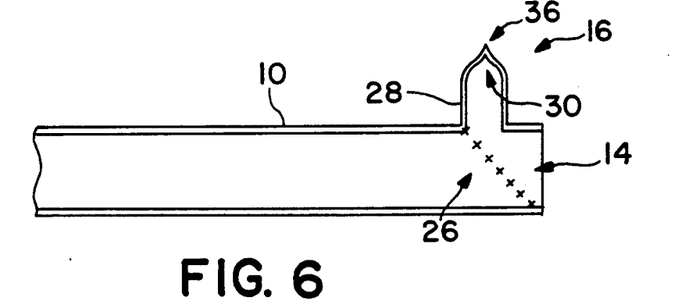
FIG. 6 is a side schematic view of another embodiment of the bubble elimination port of the present invention, including a one-way valve.

FIG. 6 illustrates another embodiment of bubble elimination port 16, wherein vent 30 is normally closed by a one-way valve 36. In this configuration a clinician can be assured that no air or other environmental elements will be introduced to the fluid circuit through bubble elimination port 16 during either the priming stage or the connecting stage. In addition to allowing for a smaller sized bubble elimination port 16, this embodiment has particular utility where port 16 is formed of a flexible material, and can be vented merely by pinching or occluding chamber body 28. Moreover, it will be appreciated that repeated or successive venting of chamber body 28 through vent 30 thus can create a vacuum that will suck fluid and any further bubbles into chamber body 28 from the fluid circuit, in a manner similar to the "roll-up" procedure, to assure a bubble-free connection. One example of a one-way valve is a duck-bill valve, which is self-closing and, thus, facilitates easy operation by a single clinician.

Figure 7:
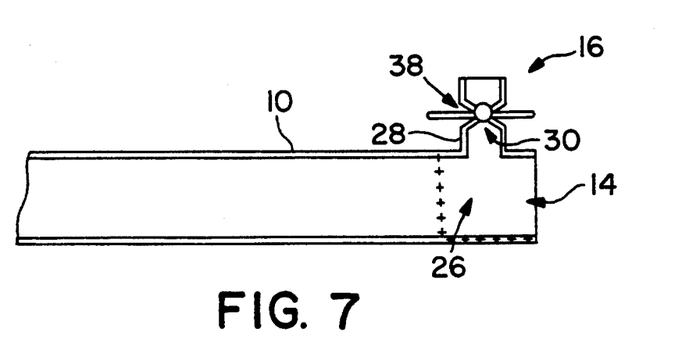
FIG. 7 is a side schematic view of another embodiment of the bubble elimination port of the present invention, including a two-way valve.

FIG. 7 illustrates yet another embodiment of bubble elimination port 16, wherein vent 30 comprises a two-way valve 38. For example, as shown in FIG. 7, two-way valve 38 may be a stop-cock. In this configuration, a clinician can vent to the external environment any bubbles collected in bubble elimination port 16 during either the priming stage or the connecting stage. Also, during the connecting stage two-way valve 38 may be utilized to introduce any desired fluids or medication prior to the final stage where tubes 10,12 are connected in a continuous, fluid-tight circuit (see FIG. 3).

In each of the above embodiments, bubble elimination port 16 is formed as an integral portion of first tube 16, and remains a portion of the connected system. However, bubble elimination port 16 may be designed to be removable from the system after the final stage of connection is completed. For example, bubble elimination port 16 may be removed by cutting it off with a knife. Alternatively, an overlapping portion of first tube 10 may be provided with a score line, as variously shown in phantom in FIGS. 4 to 7, and bubble elimination port 16 may be removed by ripping or pulling it free of first tube 10. Moreover, although only the protruding portion need be removed to prevent accidental or inadvertent catching of the port during procedure, it will be appreciated that removal of the entire overlapping portion of first tube 10, that is, the portion distal of the annular seal formed with barbs 22, will facilitate viewing of the continuous fluid channel to assure a bubble-free connection.

Figure 8:
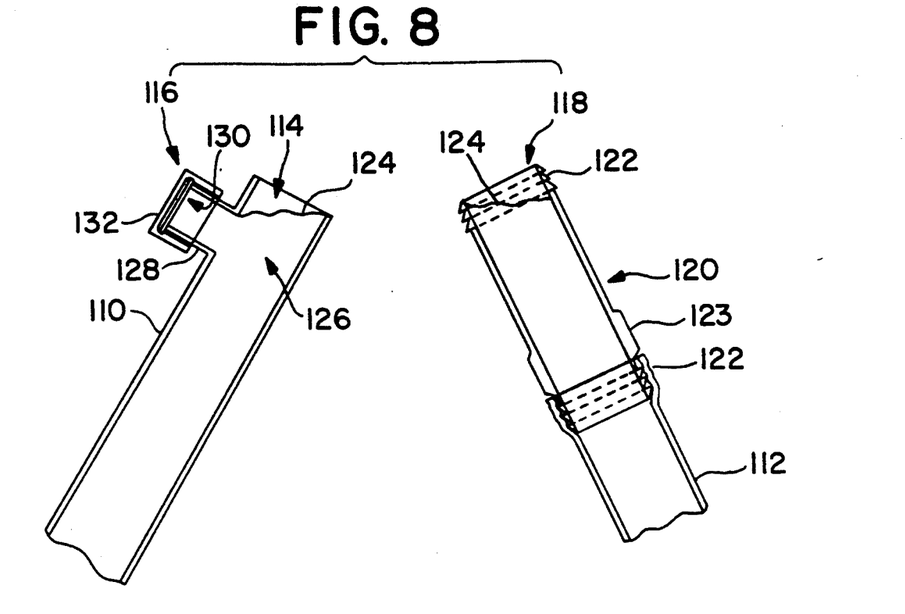
FIG. 8 is a side schematic view of another embodiment of a connector system of the present invention including a connector tube.
Figure 9:
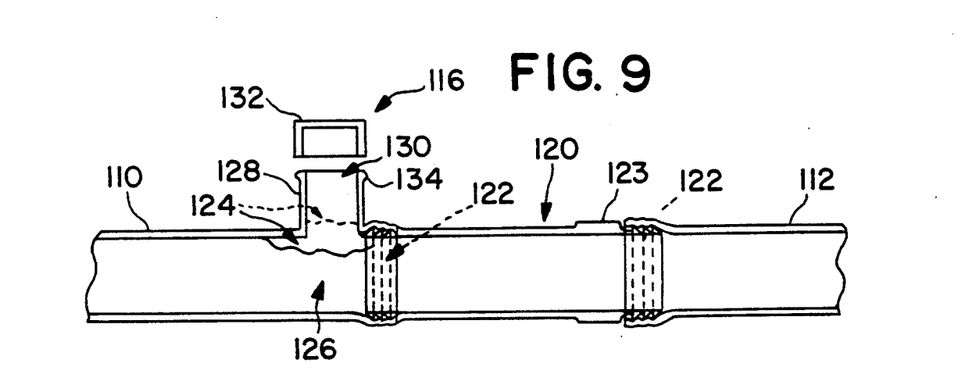
FIG. 9 is a side schematic view of the connector system of FIG. 8, wherein the connector tube is inserted to a first position, and a bubble elimination port of the first tube is open to a fluid-tight circuit.
Figure 10:
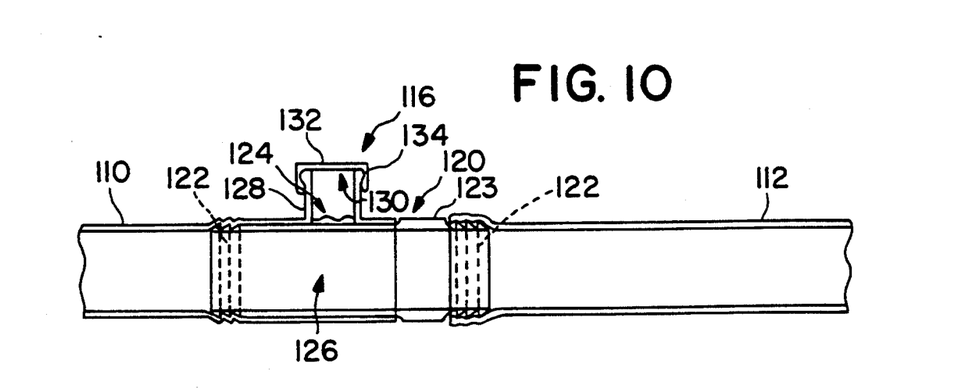
FIG. 10 is a side view of the connector system of FIG. 8, wherein the connector tube is inserted to a second position, and a bubble elimination port of the first tube is closed to a continuous, fluid-tight circuit.

FIGS. 8 to 10 illustrate another embodiment of a bubble-free connector system of the present invention. In this embodiment, the system includes a first tube 110, a second tube 112, and a connector tube 120. As in the previous embodiment, first tube 110 has an open end 114 and a bubble elimination port 116 disposed proximate open end 114. Second tube 112 has an open end 118.

The size, composition and arrangement of tube 110, open end 114 and bubble elimination portion 116 may be the same as the corresponding elements in the embodiment of FIGS. 1 to 3, except that port 116 includes a vent 130 and cap 132 arrangement as shown in FIG. 5. Of course, one skilled in the art readily will appreciate that these characteristics may be varied and modified to accommodate numerous applications.

The size, composition and arrangement of second tube 112 also may be varied and modified to accommodate numerous applications. However, the sizing and the composition of second tube 112 generally will be the same as, or comparable to, that of first tube 110.

Connector tube 120 is sized and configured to be inserted into tubes 110,112 to provide a continuous fluid channel or circuit. In the present embodiment, connector tube 120 is a ⅜ inch inner diameter—9/16 inch outer diameter tube, and is about 3 inches long. Connector tube 120 may include one or more annular ridges or barbs 122 proximate each end thereof to provide for a secure but removable connection between such ends and open ends 114,118 of first and second tubes 110,112.

For example, as shown in FIGS. 8 to 10, connector tube 120 may have 2 sets of 3 barbs located in respective ¼ inch long portions adjacent each end thereof. As in the previous embodiment, it will be appreciated that annular barbs 122 will form an annular, fluid-tight seal with the respective inner walls of first and second tubes 110,112. Connector tube 120 also may include an annular grip 123 to facilitate manipulation by a clinician. Finally, connector tube 120 preferable is composed of a clear, rigid material suitable for carrying blood, and most preferably is composed of polypropylene, to facilitate viewing by the clinician during the bubble elimination stage.

The method for using the system of FIGS. 8 to 10 is substantially similar to that of the embodiment of FIGS. 1 to 3. Specifically, in the present embodiment, one end of connector tube 120 first is inserted into open end 118 of second tube 112. In this manner, as shown in FIG. 8 (priming stage), connector tube 120 forms an extension of second tube 112, including a connector portion (connector tube 120) for effecting a fluid-tight connection between first tube 110 and second tube 112. Thus, it will be appreciated that this embodiment has particular utility in applications where tube 112 is a standard tubing.

Referring now to FIG. 9, in a connecting stage the open end of connector tube 120 is inserted into open end 114 of first tube 110 to form an annular, fluid-tight seal between barbs 122 of connector tube 120 and first tube 110 at open end 114. As in the previous embodiment, in the first position, bubble elimination port 116 is open to a closed, fluid-tight channel or circuit. As shown therein, during this connecting stage, a bubble may be formed in the fluid circuit. However, any bubble may be removed from the fluid circuit to bubble elimination port 116 by a well known method, such as by tapping the tubing.

In a case where the volume of a bubble is greater than the volume of bubble elimination port 116, as shown in FIG. 9, cap 132 may be removed to allow the bubble to escape to the external environment. In this manner, any bubble in the fluid circuit may be removed. Moreover, as a bubble is removed to the external environment, a small amount of fluid from the fluid circuit may be biased into bubble elimination port 116 as shown by dotted lines in FIG. 9, by conventional means, such as a roll-up technique, or by pinching second tube 112, to insure that the fluid channel or circuit is bubble-free.

Referring now to FIG. 10, in a final stage connector tube 120 is further inserted into the first tube 110 to a second position, to form an annular, fluid-tight seal upstream of bubble elimination port 116. As shown therein, bubble elimination port 116 is closed to a continuous, fluid-tight channel or circuit, that is, without forming any discontinuities in the fluid circuit that may tend to cause thrombus.

Figure 11:
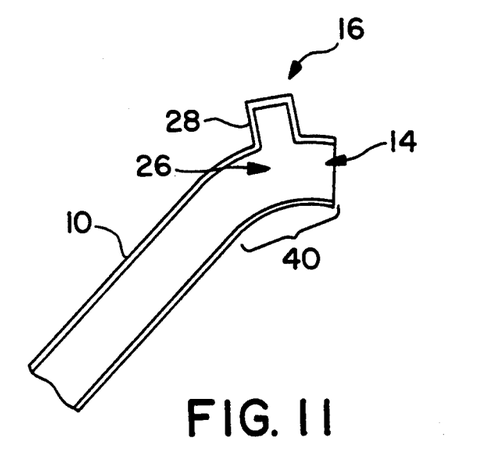
FIG. 11 is a side schematic view of an alternative embodiment of a first tube of the connector system of the present invention having a curved portion formed proximate an open end thereof, and including a bubble elimination port located on the curved portion.

FIG. 11 illustrates an alternative embodiment of a first tube 10 of the present invention. In this embodiment, first tube 10 is composed of a flexible material, such as PVC or the like, and has a curved portion 40 proximate open end 14. Bubble elimination port 16 is located on curved portion 40, preferably at a high point thereof. In this manner, it will be appreciated that any bubbles formed in the fluid circuit during either the priming stage or the connecting stage inherently will tend to rise to the high point, and into bubble elimination port 16. Thus, bubble elimination is facilitated. Moreover, since first tube 10 is formed of a flexible material, it will be appreciated that, as the connector portion or tube is inserted into first tube 10 to the second position, will cause curved portion 40 to conform to the configuration thereof, e.g., to straighten out. In this manner, the connector portion or tube is less likely to become accidentally disconnected from tube 10 during procedure. In order to further facilitate insertion, a portion of first tube 10 proximate open end 14 may be pretreated. For example, the curved portion may be prestretched. Alternatively, first tube 10 may be formed of a heat sensitive material, and the portion proximate open end 14 can be preheated to soften it.

Figure 12:
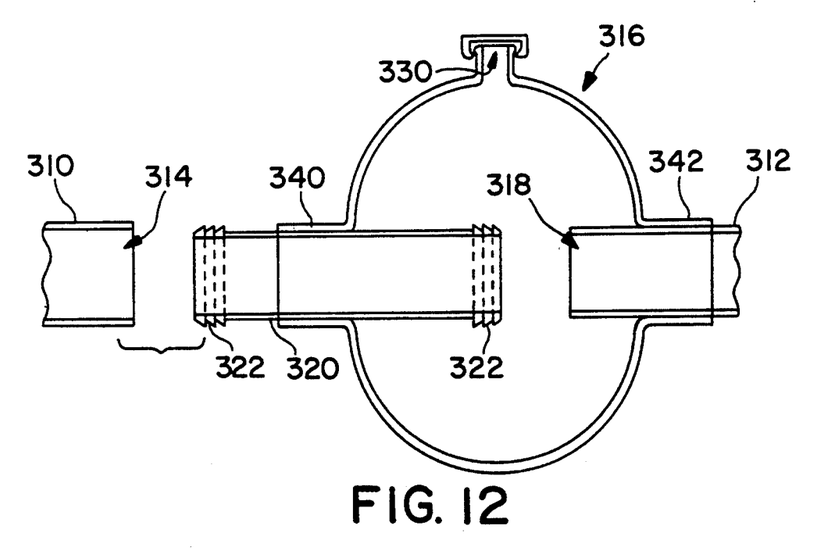
FIG. 12 is a side schematic view of a third embodiment of a connector system of the present invention including a connector tube and balloon system.

FIG. 12 illustrates in side schematic view a third embodiment of a connector system of the present invention. In this embodiment, the system generally includes a first tube 310, a second tube 312 and means for connecting tubes 310,312 in a continuous, bubble-free fluid circuit. Specifically, in the embodiment of FIG. 12, the connecting means includes a bubble elimination balloon 316 and a connector tube 320.

The size, composition and configuration of first tube 310, second tube 312 and connector tube 320 generally is the same as that in the embodiment of FIGS. 8 to 10, except that first tube 310 is not provided with a bubble elimination port. Rather, the system is provided with a bubble elimination balloon 316. Balloon 316 is provided with a first connecting port 340 for connecting to connector tube 320, and a second connecting port 342 for connecting to first tube 310. Specifically, each connecting port 340,342 may be a stretchable annular or tubular opening which forms a fluid-tight seal, respectively, with connector tube 320 and first tube 310. For example, in the embodiment of FIG. 12, balloon 316 is composed of a latex material.

In one method for using the system of FIG. 12, connecting ports 340,342 are connected, respectively, to connector tube 320 and to first tube 310, as shown in FIG. 12. The subsequent stages of the present connecting procedure are similar to the above-described procedures. The open end of connector tube 320 is inserted into second tube 312 to form an extension or connector portion thereof. Upon this connection, it will be appreciated that tubes 310,312 connector 320 and balloon 316 form a fluid-tight circuit. Thus, at this time the priming stage can be carried out without worry of any prime fluid spilling from the circuit. Specifically, in the priming stage of the present embodiment, prime fluid is introduced through one or both of tubes 310,312 until balloon 316 is filled sufficiently that open end 314 of first tube 310 and the free open end of connector tube 320 are submerged in prime fluid 324, and any bubbles formed therein are removed to bubble elimination balloon 316. During this stage, bubble elimination balloon 316 may be drained/deflated through a vent 330, such as a luer valve, etc., so that balloon 316 does not become overstretched. Then, the open end of connector tube 320 may be inserted into open end 314 of first tube 310 to form a continuous, bubble-free fluid channel or circuit. Thereafter, bubble elimination balloon 316 may be drained through vent 330 so that bubble elimination balloon 316 does not create a significant protrusion. Alternatively, balloon 316 may be cut or torn away, to eliminate any protrusion from the fluid circuit.

Although the present invention has been described with respect to several specific embodiments and applications, it is not limited thereto. Numerous variations and modifications readily will be appreciated by those skilled in the art and are intended to be included within the scope of the present invention, which is recited in the following claims.

What we claim is:

1. A system for connecting two liquid carrying tubes, including means for permitting escape of a gas bubble therefrom, the system comprising:
   a first tube having an axis, a lumen therethrough, an open end, and a bubble elimination port formed in a wall of said first tube, axially displaced from the open end of said first tube and in fluid communication with the lumen of said first tube;
   a second tube having a lumen therethrough and an open end;
   means for connecting the first and second tubes in a first position, with the open ends of the first and second tubes forming a fluid-tight connection, the lumen of said first tube and the lumen of said second tube forming a continuous fluid circuit, and the bubble eliminated port being open to the continuous fluid circuit to permit escape of said gas bubble from the continuous fluid circuit; and
   means for connecting the first and second tubes in a second position, the lumen of said first tube and the lumen of said second tube forming a continuous fluid-tight circuit, and the bubble elimination port being closed by said second tube.

2. The system of claim 1, wherein said connecting means comprises a connector portion formed at the open end of said second tube for forming a fluid-tight connection between said first tube and said second tube when said first and second tubes are connected in the first position or in the second position.

3. The system of claim 2, wherein said connector portion is insertable in the lumen of said first tube to connect said first and second tubes in the first position or the second position.

4. The system of claim 3, wherein said connector portion comprises at least one annular ridge proximate the open end of said second tube.

5. The system of claim 4, wherein the connector portion has three annular ridges.

6. The system of claim 3, wherein said connector portion comprises a lubricated portion for facilitating insertion thereof into said first tube.

7. The system of claim 4, wherein said connector portion comprises a lubricated portion for facilitating insertion thereof into the first tube, said lubricated portion being adjacent said at least one annular ridge.

8. A method for using the system of claim 1, comprising the steps of:
   priming the first and second tubes
   connecting said first and second tubes in a first position so that the open end of said first tube and the open end of said second tube form a fluid-tight connection and the lumen of said first tube and the lumen of said second tube form a continuous fluid circuit, and the bubble elimination port is open to the fluid circuit to permit escape of said gas bubble from the fluid circuit;
   eliminating said gas bubble from the fluid circuit by removing said gas bubble through the bubble elimination port; and
   connecting said first and second tubes in a second position, the lumen of said first tube and the lumen of said second tube forming a continuous fluid-tight circuit, and the bubble elimination port being closed.

9. The system of claim 1, wherein said first tube comprises a curved portion proximate the open end thereof.

10. The system of claim 9, wherein the bubble elimination port is located at a high point of said curved portion.

11. The system of claim 9, wherein at least said curved portion of said first tube is composed of a flexible material.

12. The system of claim 11, wherein said connecting means comprises a connector portion, and wherein said curved portion conforms to a configuration of said connector portion when the connecting means is in the second position.

13. The system of claim 12, wherein said connector portion is straight.

14. The system of claim 1 wherein said bubble collection chamber has a volume in a range of about 0.5 to 2 cc.

15. The system of claim 1, wherein said first tube comprises a-pretreated portion proximate the open end thereof, for facilitating connection with said second tube.

16. The system of claim 15, wherein the pretreated portion is prestretched.

17. The system of claim 15, wherein the pretreated portion is preheated.

18. The system of claim 1, wherein said bubble elimination port comprises a bubble collection chamber.

19. The system of claim 1, wherein said bubble elimination port communicates with the external environment.

20. The system of claim 19, wherein said bubble elimination port is provided with a cap.

21. The system of claim 19, wherein said bubble elimination port is provided with a one-way valve.

22. The system of claim 19, wherein said bubble elimination port is provide with a two-way valve.

23. The system of claim 1, wherein said bubble elimination port is detachable from said first tube.

24. The system of claim 1, wherein said connecting means comprises a connector tube having a lumen therethrough forming first and second open ends thereof, said first and second open ends being insertable into said first and second tubes, respectively.

25. The system of claim 23, wherein one open end of said connector tube is insertable in the open end of said second tube, and the other open end of said connector tube is insertable in the open end of said first tube to connect the first and second tubes in the first and second positions.

26. The system of claim 23, wherein said connector tube has at least one annular ridge proximate at least one open end of said connector tube.

27. The system of claim 23, wherein said connector tube has at least one annular ridge proximate each of said open ends of said connector tube.

28. The system of claim 26, wherein the number of annular ridges at each open end is three.

29. The system of claim 24, wherein said connector tube comprises a lubricated portion for facilitating insertion thereof into one of said first and second tubes.

30. The system of claim 24, wherein said connector tube comprises a lubricated portion for facilitating insertion thereof into said first tube.

31. The system of claim 24, wherein said connector tube is rigid, wherein said first tube comprises a curved portion proximate the open end thereof, and at least said curved portion is composed of a flexible material, and wherein said curved portion conforms to a configuration of said connector tube when the connecting means is in the second position.

32. The system of claim 31, wherein the bubble elimination port is located at a high point of said curved portion.

33. A method for using the system of claim 24, comprising the steps of:
- inserting one end of the connector tube in the open end of the second tube;
- priming the first and second tubes and the connector tube;
- inserting the other end of the connector tube into the open end of the first tube to a first position, wherein the bubble elimination port is open to the fluid circuit;
- eliminating said gas bubble from the fluid circuit by removing said gas bubble to the bubble elimination port; and
- further inserting the connector tube into the first tube to a second position, wherein the bubble elimination port is closed.

34. A system for connecting two blood carrying tubes, including means for permitting escape of an air bubble therefrom, to prevent an embolism in the blood stream, the system comprising:
- a first tube having an axis, a lumen therethrough, an open end, and a bubble elimination port formed in a wall of said first tube axially displaced from the open end of said first tube and in fluid communication with the lumen of said first tube;
- a second tube having a lumen therethrough and an open end;
- means for connecting the first and second tubes in a first position, with the open ends of the first and second tubes forming a fluid-tight connection, whereby the lumen of said first tube and the lumen of said second tube form a continuous fluid circuit, and the bubble elimination port is open to the continuous fluid circuit to permit escape of said air bubble from the continuous fluid circuit; and
- means for connecting the first and second tubes in a second position, so that the lumen of said first tube and the lumen of said second tube form a continuous fluid-tight circuit, and the bubble elimination port is closed by said second tube.

* * * * *